(12) United States Patent
Potasek et al.

(10) Patent No.: US 11,513,091 B2
(45) Date of Patent: Nov. 29, 2022

(54) GAS DETECTION DEVICE AND METHOD OF MANUFACTURING THE SAME

(71) Applicant: Carrier Corporation, Palm Beach Gardens, FL (US)

(72) Inventors: David P. Potasek, Lakeville, MN (US); John Carl Christenson, Prior Lake, MN (US); Roger Alan Backman, Minneapolis, MN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 1038 days.

(21) Appl. No.: 16/304,878

(22) PCT Filed: May 17, 2017

(86) PCT No.: PCT/US2017/033158
§ 371 (c)(1),
(2) Date: Nov. 27, 2018

(87) PCT Pub. No.: WO2017/205146
PCT Pub. Date: Nov. 30, 2017

(65) Prior Publication Data
US 2020/0326295 A1   Oct. 15, 2020

Related U.S. Application Data

(60) Provisional application No. 62/342,531, filed on May 27, 2016.

(51) Int. Cl.
*G01N 27/12* (2006.01)
*G01N 33/00* (2006.01)
*H01L 21/768* (2006.01)

(52) U.S. Cl.
CPC .......... *G01N 27/12* (2013.01); *G01N 33/004* (2013.01); *G01N 33/006* (2013.01); *G01N 33/0044* (2013.01); *H01L 21/7685* (2013.01)

(58) Field of Classification Search
CPC .......... B81B 2201/0214; G01N 27/125; G01N 2027/222; G01N 27/221; G01N 27/041; G01N 27/128; G01N 27/4141
See application file for complete search history.

(56) References Cited

U.S. PATENT DOCUMENTS

| 4,224,280 A | * | 9/1980 | Takahama | G01N 27/12 73/31.06 |
| 4,387,165 A | | 6/1983 | Youngblood | |

(Continued)

FOREIGN PATENT DOCUMENTS

| CN | 102778481 B | * | 6/2014 |
| DE | 60004843 T2 | * | 6/2004 |

(Continued)

OTHER PUBLICATIONS

International Search Report and Written Opinion for application PCT/US2017/033158, dated Aug. 21, 2017, 11 pages.

*Primary Examiner* — David A. Rogers
(74) *Attorney, Agent, or Firm* — Cantor Colburn LLP

(57) ABSTRACT

A gas detection device is provided. The device includes a substrate and a dielectric material applied to the substrate. A sensor material is applied to the dielectric film. The sensor material has a bottom, a side, and a top surface. An electrode material is at least partially applied to the dielectric film and at least partially applied to a portion of the side of the sensor material and a portion of the top surface of the sensor material to pin a portion of the sensor material to the dielectric material. The electrode material forms a vapor barrier upon the sensor material to facilitate preventing delamination between the sensor material and the electrode material over portions of the sensor material where the sensor material is not pinned to the dielectric material.

19 Claims, 7 Drawing Sheets

(56) References Cited

U.S. PATENT DOCUMENTS

| | | | |
|---|---|---|---|
| 4,399,424 A * | 8/1983 | Rigby | G01N 27/12 338/308 |
| 4,840,913 A * | 6/1989 | Logothetis | G01N 27/12 436/118 |
| 5,250,170 A | 10/1993 | Yagawara et al. | |
| 5,360,528 A * | 11/1994 | Oh | G01N 27/419 204/426 |
| 5,693,577 A * | 12/1997 | Krenik | G01N 27/12 148/DIG. 52 |
| 6,022,754 A * | 2/2000 | Guillemet | G01N 27/12 438/49 |
| 6,090,436 A * | 7/2000 | Miyoshi | H01B 1/16 427/376.6 |
| 6,297,138 B1 | 10/2001 | Rimai et al. | |
| 6,311,545 B1 | 11/2001 | Tamaki et al. | |
| 6,418,784 B1 | 7/2002 | Samman et al. | |
| 6,746,960 B2 * | 6/2004 | Goodman | G01N 33/0031 422/50 |
| 6,777,024 B2 * | 8/2004 | Hattori | G01N 27/12 427/126.3 |
| 7,749,791 B2 | 7/2010 | Ishida et al. | |
| 7,955,561 B2 | 6/2011 | Lewis et al. | |
| 8,052,932 B2 * | 11/2011 | Han | G01N 27/127 324/693 |
| 8,383,048 B2 | 2/2013 | Van Hal et al. | |
| 8,573,030 B2 | 11/2013 | Gole | |
| 8,582,099 B2 | 11/2013 | Guo et al. | |
| 8,683,672 B2 | 4/2014 | Deshusses et al. | |
| 8,778,714 B2 * | 7/2014 | Trakhtenberg | G01N 27/127 427/126.3 |
| 9,157,879 B2 * | 10/2015 | Kenning | B82Y 30/00 |
| 9,285,349 B2 | 3/2016 | Chen | |
| 9,598,282 B2 * | 3/2017 | Han | B82Y 15/00 |
| 9,664,633 B2 * | 5/2017 | Erdler | G01N 27/12 |
| 9,748,482 B2 * | 8/2017 | Zan | G01N 27/125 |
| 10,011,481 B2 * | 7/2018 | Haick | G01N 27/4148 |
| 10,054,562 B2 * | 8/2018 | Shalev | H01L 21/22 |
| 10,352,726 B2 * | 7/2019 | Giedd | G01D 5/16 |
| 10,379,072 B2 * | 8/2019 | Blease | G01N 27/126 |
| 10,656,129 B2 * | 5/2020 | Hsueh | G01N 27/12 |
| 10,852,269 B2 * | 12/2020 | Yamada | G01N 27/4076 |
| 10,871,462 B2 * | 12/2020 | Alberti | B81B 3/0089 |
| 10,914,702 B2 * | 2/2021 | Schreivogel | G01N 27/221 |
| 10,942,157 B2 * | 3/2021 | Brahem | G01N 27/021 |
| 11,073,491 B2 * | 7/2021 | Hashizume | G01N 27/126 |
| 11,243,186 B2 * | 2/2022 | Haick | G01N 33/54373 |
| 2003/0099575 A1 | 5/2003 | Sung et al. | |
| 2005/0097941 A1 * | 5/2005 | Sandvik | G01N 27/4141 73/31.06 |
| 2007/0095678 A1 * | 5/2007 | West | G01N 27/126 205/775 |
| 2008/0116490 A1 * | 5/2008 | Stewart | G01N 27/128 257/210 |
| 2008/0157152 A1 * | 7/2008 | Shim | H01L 27/14609 257/292 |
| 2009/0058431 A1 * | 3/2009 | Dass | G01N 27/12 324/693 |
| 2009/0312954 A1 | 12/2009 | Utriainen | |
| 2010/0112546 A1 * | 5/2010 | Lieber | G01N 33/6854 530/391.1 |
| 2010/0133642 A1 * | 6/2010 | Choi | H01L 27/14687 257/E31.11 |
| 2010/0144059 A1 * | 6/2010 | Frisk | G01N 33/54366 204/627 |
| 2011/0076185 A1 | 3/2011 | Hammond et al. | |
| 2013/0043552 A1 * | 2/2013 | Lazarov | G01J 5/0803 257/E31.127 |
| 2014/0138259 A1 | 5/2014 | Mickelson et al. | |
| 2014/0197046 A1 | 7/2014 | Busnaina et al. | |
| 2016/0018356 A1 * | 1/2016 | Shankar | G01N 27/128 438/49 |
| 2016/0018371 A1 | 1/2016 | Acharya et al. | |
| 2016/0069810 A1 | 3/2016 | Walavalkar et al. | |
| 2017/0016866 A1 * | 1/2017 | Chey | C23C 14/34 |
| 2017/0356869 A1 * | 12/2017 | Koenig | G01N 27/121 |
| 2019/0128830 A1 * | 5/2019 | Alberti | G01N 27/127 |
| 2019/0178860 A1 * | 6/2019 | Hsueh | G01N 27/123 |
| 2019/0234896 A1 * | 8/2019 | Andersson | G01N 33/0014 |
| 2020/0254452 A1 * | 8/2020 | Erramilli | G01N 27/4148 |
| 2020/0326295 A1 * | 10/2020 | Potasek | H01L 21/7685 |
| 2020/0371056 A1 * | 11/2020 | Lai | G01N 33/004 |
| 2021/0181172 A1 * | 6/2021 | Ensor | B82Y 30/00 |
| 2021/0311006 A1 * | 10/2021 | Rogers | G01N 33/0013 |

FOREIGN PATENT DOCUMENTS

| | | | | |
|---|---|---|---|---|
| EP | 0795747 A1 | | 9/1997 | |
| GB | 2085168 A | * | 4/1982 | G01N 27/12 |
| GB | 2202948 A | * | 10/1988 | G01N 27/12 |
| JP | 01259250 A | * | 10/1989 | |
| KR | 20090059473 A | * | 6/2009 | |
| WO | WO-2008058553 A1 | * | 5/2008 | G01N 27/125 |
| WO | WO-2019175566 A1 | * | 9/2019 | G01N 27/125 |

* cited by examiner

GAS DETECTION DEVICE AND METHOD OF MANUFACTURING THE SAME

CROSS REFERENCE TO RELATED APPLICATION

The present application is an international patent application, which claims the priority benefit of U.S. Application Ser. No. 62/364,654, filed May 27, 2016, which is herein incorporated in its entirety.

TECHNICAL FIELD OF THE DISCLOSED EMBODIMENTS

The presently disclosed embodiments generally relate to gas detection devices, and more particularly, to a system and method for improving the durability of a gas detection device.

BACKGROUND OF THE DISCLOSED EMBODIMENTS

Generally, gas detection devices are chemo-resistive devices. The gas detection devices change electrical resistance upon contact with a target gas. In some situations, the gas detection device operates in a high humidity environment, wherein the gas detection device absorbs atmospheric moisture. As the gas detection device absorbs atmospheric moisture the sensor element in the gas detection device expands. The sensor element may exhibit a volume expansion of nearly 50% in the presence of water or high humidity. The volume expansion of the sensor element can cause a delamination of the sensor element from the electrode material and other materials in the gas detection device.

Additionally, gas detection devices typically operate at high temperatures, temperatures often above the boiling point of water. These high temperatures can drive the absorbed water from the sensor element. As water is driven out of the sensor element, the sensor element experiences a volume contraction, which can cause delamination of the sensor element from the electrode material and other materials in the gas detection device. Cycling volume expansion and volume contraction, even if it is not excessive, can cause delamination. Generally, once fabricated, gas detection devices may be sealed in a dry environment in a container with a desiccant, or run at its operating temperature to prevent the absorption of water into the sensor element and the resultant delamination.

Generally, a gas detection device may be fabricated upon a silicon substrate. Common materials from which the electrodes may be made in the gas detection device include a metal, such as gold or other metals such as aluminum, and polysilicon. Common dielectric films that may be used in the construction of gas detection devices include silicon nitrides and silicon oxides. The substrate may advantageously be processed such that all manufacturing processes completed on the substrate are done prior to the sensor element deposition. Generally, a gas detection device that uses a sensing material such as tin dioxide on top of the substrate needs to be exposed to the environment, which may be moisture rich, to sense the target gas.

Gas detection devices typically have an electrode material deposited immediately prior to the sensor element. When there is a volume expansion or contraction of the sensor element material with respect to the electrode material, the volume expansion and contraction can cause the delamination of the electrode from the sensor element due to the large compressive or tensile, respectively, forces. For instance, the delamination of the electrode material from the tin dioxide sensor material in a MOS (Metal Oxide Semiconductor) sensor element may destroy the gas sensor.

Delamination may cause a field failure of a gas detection device. In the case of a gas sensor using tin dioxide as the MOS sensor material, volume expansion of the tin dioxide layer caused by exposure to and absorption of moisture, and volume contraction of the tin dioxide layer caused by desorption of moisture from the tin dioxide layer may cause the tin dioxide-electrode interface to fail. The same volume expansions or contractions of the tin dioxide layer will not cause the tin dioxide-nitride interface to fail. The tin dioxide remains adhered to the nitride. This is because the nitride-tin dioxide interface is stronger than the moisture-induced strain of the tin dioxide. There are processing complications from applying and patterning the electrode material after the sense material. Many processes known in the art for depositing and patterning an electrode material, such as gold, for instance, involve wet processes. Importantly, a sensor element should not be exposed to water during processing due to potential volume expansion or contraction delamination failures.

A need remains for preventing delamination between the sensor element and the electrode material.

SUMMARY OF THE DISCLOSED EMBODIMENTS

In one aspect, a gas detection device is provided. The device includes a substrate and a dielectric material applied to the substrate. A sensor material is applied to the dielectric film. The sensor material has a bottom, a side, and a top surface. An electrode material is at least partially applied to the dielectric film and at least partially applied to a portion of the side of the sensor material and a portion of the top surface of the sensor material to pin a portion of the sensor material to the dielectric material. The electrode material forms a vapor barrier upon the sensor material to facilitate preventing delamination between the sensor material and the electrode material over portions of the sensor material where the sensor material is not pinned to the dielectric material.

In a further aspect of the above, the vapor barrier is formed by the electrode material on the portion of the side of the sensor material and the portion of the top surface of the sensor material where the electrode material is applied.

In a further aspect of any of the above, the electrode material is at least partially applied to a portion of the bottom of the sensor material. The vapor barrier is formed by the electrode material on the portion of the bottom of the sensor material where the electrode material is applied.

In a further aspect of any of the above, the electrode material substantially encloses portions of the sensor material which are not pinned to the dielectric layer, wherein the electrode material mitigates the volume expansion or contraction of the portions of the sensor material enclosed by the electrode material.

In a further aspect of any of the above, the electrode material is constructed and arranged to deform with the volume expansion or contraction of the sensor material without causing the delamination of the electrode material from the sensor material.

In a further aspect of any of the above, the electrode material is constructed and arranged to remain in contact with the sensor material during volume expansion or contraction of the sensor material.

In a further aspect of any of the above, an adhesion layer is applied during a deposition process with the electrode material without breaking a vacuum formed during the deposition process and without interrupting the deposition process.

In a further aspect of any of the above, the electrode material is formed without the use of water, water-based compounds, or saturating materials after the sensor material has been formed upon the substrate.

In one aspect, a method of forming a gas detection device is provided, wherein the method include applying a dielectric material to a substrate. The method also includes applying a sensor material to the dielectric film. The sensor material has a bottom, a side, and a top surface. The method also include at least partially applying an electrode material to the dielectric film and a portion of the side of the sensor material and a portion of the top surface of the sensor material to pin a portion of the sensor material to the dielectric material. The electrode material forms a vapor barrier upon the sensor material to facilitate preventing delamination between the sensor material and the electrode material over portions of the sensor material where the sensor material is not pinned to the dielectric material.

In a further aspect of the above, the method also includes forming the vapor barrier with the electrode material on the portion of the side of the sensor material and the portion of the top surface of the sensor material where the electrode material is applied.

In a further aspect of any of the above, the method also includes at least partially applying the electrode material to a portion of the bottom of the sensor material. The method also includes forming the vapor barrier with the electrode material on the portion of the bottom of the sensor material where the electrode material is applied.

In a further aspect of any of the above, the method also includes substantially enclosing, with the electrode material, portions of the sensor material which are not pinned to the dielectric layer, wherein the electrode material mitigates the volume expansion or contraction of the portions of the sensor material enclosed by the electrode material.

In a further aspect of any of the above, the method also includes constructing and arranging the electrode material to deform with the volume expansion or contraction of the sensor material without causing the delamination of the electrode material from the sensor material.

In a further aspect of any of the above, the method also includes constructing and arranging the electrode material to remain in contact with the sensor material during volume expansion or contraction of the sensor material.

In a further aspect of any of the above, the method also includes applying an adhesion layer during a deposition process with the electrode material without breaking a vacuum formed during the deposition process and without interrupting the deposition process.

In a further aspect of any of the above, the method also includes forming the electrode material without the use of water, water-based compounds, or saturating materials after the sensor material has been formed upon the substrate.

In a further aspect of any of the above, the method also includes forming the electrode material in more than one deposition step.

In a further aspect of any of the above, the method also includes forming at least one deposition of the electrode material after the deposition of the sensor material.

In a further aspect of any of the above, the method also includes forming at least one deposition of the electrode material after the deposition of the sensor material without the use of water, water based compounds, or saturating materials.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1:
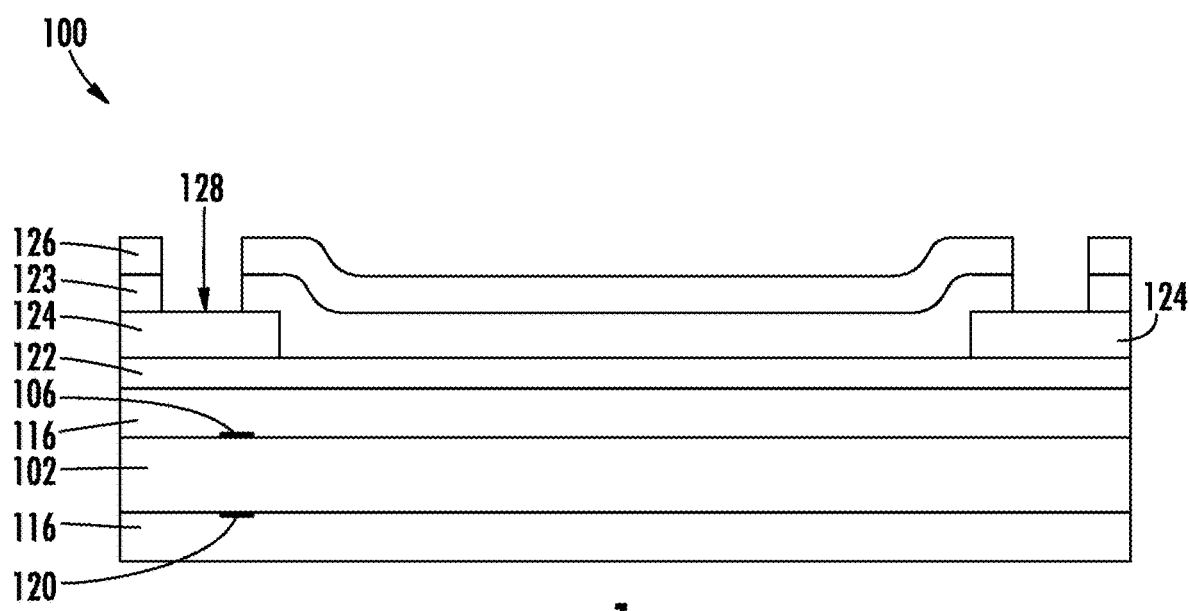
FIG. 1 is a cross sectional view of an initial base structure utilized to form a gas detector device.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 illustrates a cross sectional view of an initial base structure utilized to form a gas detector device 100. FIGS. 2-7 illustrate views of gas detector devices 100A and 100B constructed on a substrate 102. In one embodiment, the gas detector devices 100 may detect toxic gases, such as, but not limited to, hydrogen sulfide and carbon monoxide. Although the embodiments described herein are described in relation to a gas detection device, it will be appreciated by one skilled in the art that the embodiments may pertain to other detection devices or sensors, particularly devices or sensors that utilize a metal oxide for detection, or any other sets of materials with differential expansions and contractions. In one embodiment, the substrate 102 is formed from ceramic, silicon, or the like. A chemo-resistive material (i.e., sensor element) 104 (described herein with respect to FIGS. 2-7) is deposited on the substrate 102 and may be thermally and electrically isolated from its surroundings. In one embodiment, the sensor element 104 may be formed from tin oxide. The heater 124 on the gas detector device 100 may heat the sense material 104 and sense a temperature on the sensor element 104. In operation at an appropriate temperature, and under normal circumstances, the sensor element 104 generally has a high electrical resistance; however, when exposed to a specific gas, the sensor element 104 experiences a drop in resistance. This drop in resistance may be used to detect the presence of a gas in different applications. The embodiments described herein facilitate retaining the integrity of the interface between sensor element 104 and an electrode material 110 (described herein with respect to FIGS. 2-7) when the detector 100 is exposed to moisture, for example, humidity.

The methods of manufacturing the gas detectors 100 disclosed herein include methods for applying an electrode material 110 to the sensor element 104. In one embodiment, the electrode material 110 may be a noble metal, for example gold. In yet another embodiment, the electrode material 110 may be any material capable of functioning as an electrode. The methods include shadow masking the sensor element 104 onto the substrate 102 through a faceplate having apertures aligned with portions of the substrate 102 where the sensor element 104 is desired to be positioned. An electrode material 110 is then shadow masked onto the sensor element 104 through a faceplate having apertures aligned with portions of the sensor element 104 where the electrode material 110 is desired to be positioned. This method facilitates avoiding wet processing of the electrode material 110, but allows for the electrode material 110 to substantially seal the sides and portions of the top of the sensor element 104. Wet processing could ruin the sensor element 104, causing the sensor element 104 to delaminate from the electrode material 110 by volume expansion, or the sensor element 104 could be 'poisoned' by exposure to different materials, and would no longer respond to the intended target gas. In one embodiment, the methods described herein facilitate adhesion of the sensor element 104 to the substrate 102, thus mitigating the effects of sensor element moisture absorption and desorption, sensor element volume expansion and contraction, and the delamination of the sensor element 104 from the electrode material 110.

FIG. 1 illustrates part of a gas detection device 100 from which the gas detection devices 100A and 100B (described below) may be formed. A first dielectric 116, for example a dielectric film, is formed on the substrate 102 to facilitate preventing a heater 124 from electrically shorting to the substrate. The first dielectric 116 may be formed from silicon nitride or any other suitable dielectric. For example, the substrate 102 may be formed of a ceramic, of silicon, and the like, and the first dielectric 116 may be formed as a silicon oxide or a silicon nitride. In the illustrated embodiment, the first dielectric 116 is applied simultaneously to both a top surface 106 and a bottom surface 120 of the substrate 102. The first dielectric 116 may be applied to the substrate 102 using any method for applying a dielectric known in the art. A second dielectric material 122, for example a dielectric film, is then applied to the first dielectric material 116, using any method known in the art. The second dielectric material 122 may be formed from silicon oxide or any other suitable dielectric.

At least one heater 124 is coupled to dielectric layer 122. The at least one heater 124 is constructed and arranged to increase the temperature of the sensor element 104 to facilitate specific chemo-resistive reactions within the gas detection device 100. The at least one heater 124 may be coupled to the dielectric layer 122 using any method known in the art. Third and fourth dielectric layers, 123 and 126, for example dielectric films, may be applied over the at least one heater 124 and a portion of the dielectric layer 122 using any method known in the art. The third and fourth dielectric materials 123 and 126 may be formed from silicon oxide and silicon nitride, respectively, or any other suitable dielectric. In the illustrated embodiment, the dielectric materials 123 and 126 are applied, and are then etched to expose a contact 128 to the heater 124. The dielectric materials 123 and 126 may be applied using any method known in the art.

Figure 2:
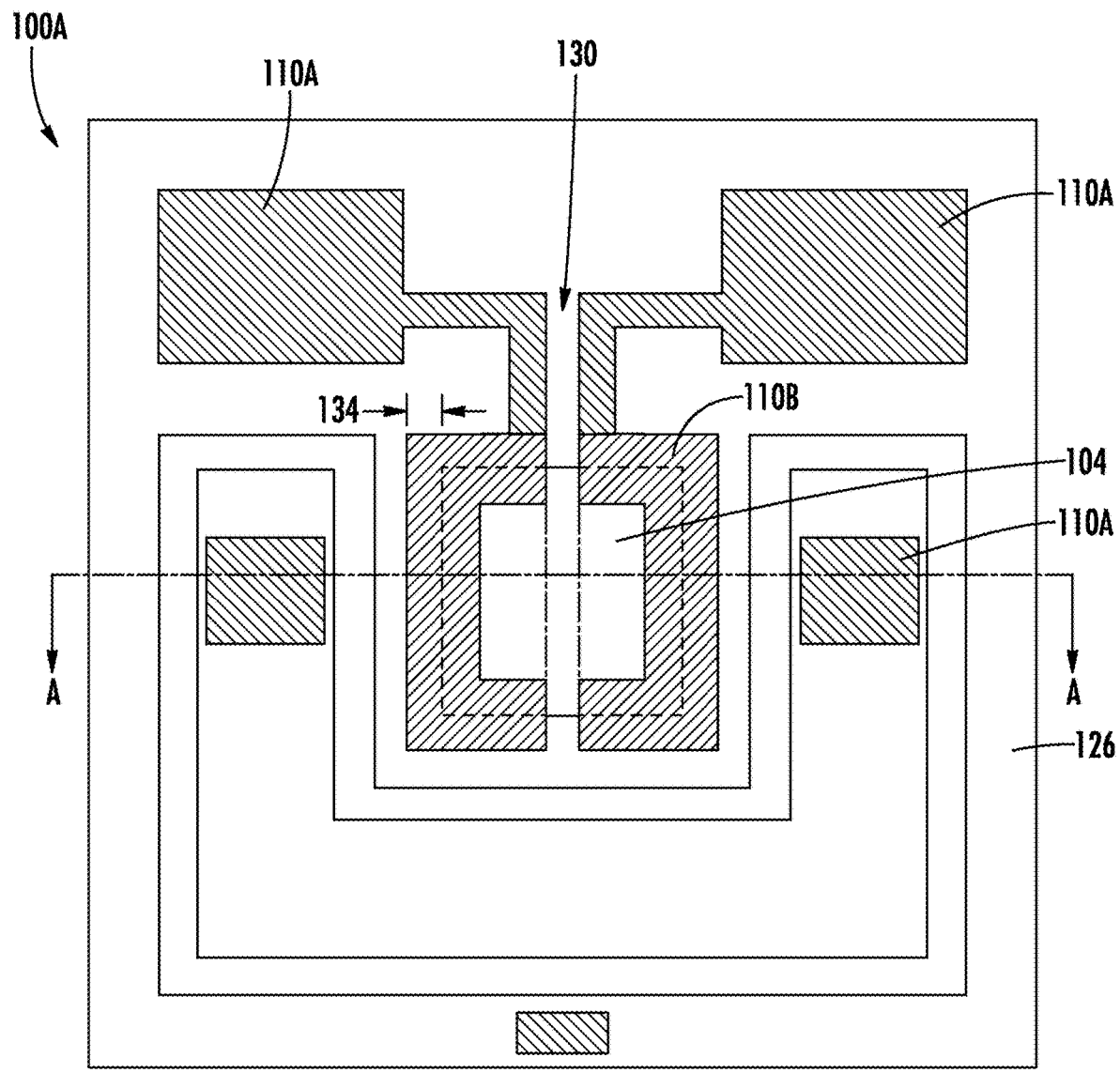
FIG. 2 is a plan view of a gas detector device formed in accordance with an embodiment.
Figure 3:
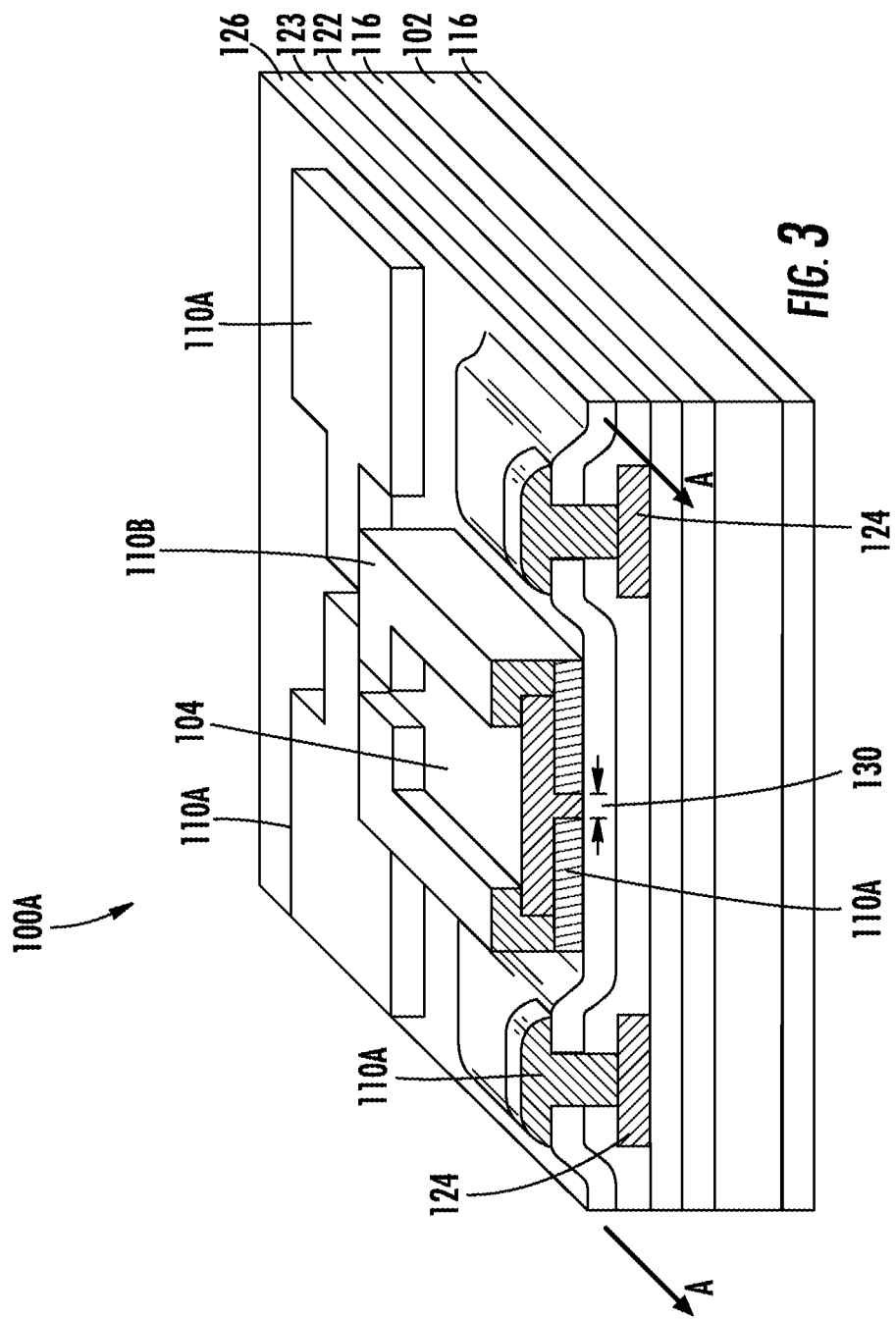
FIG. 3 is a cross sectional isometric view, taken across line A-A of FIG. 2, of a gas detector device formed in accordance with an embodiment.
Figure 4:
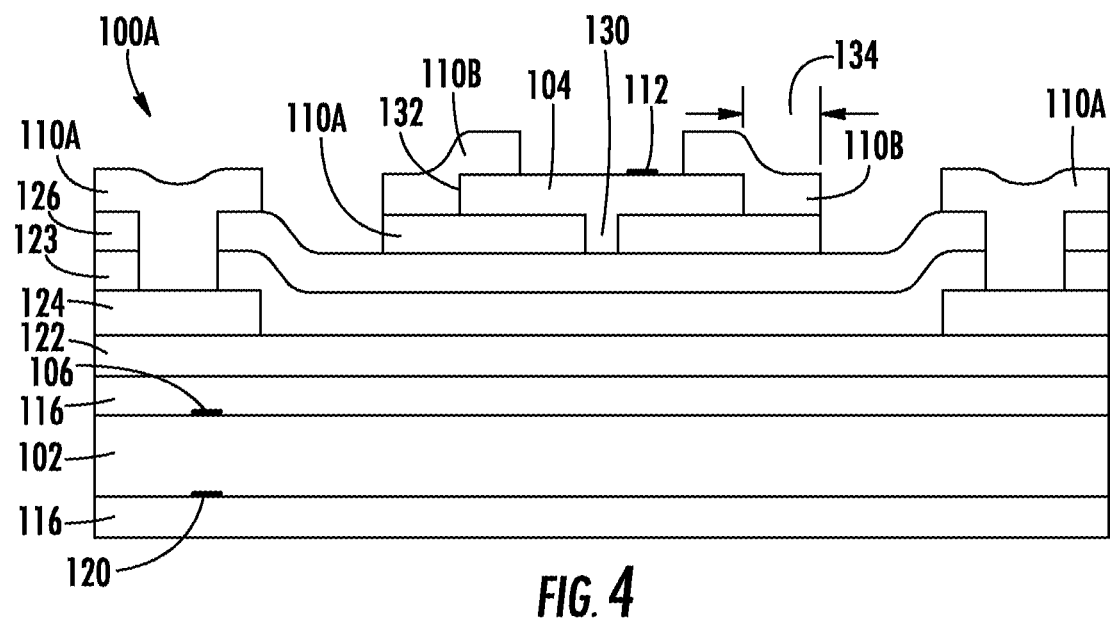
FIG. 4 is a cross sectional view, taken across line A-A of FIG. 2, of a gas detector device formed in accordance with an embodiment.

FIGS. 2-4 illustrate a gas detection device 100A formed from the initial base of the gas detection device 100 shown in FIG. 1. The gas detection device 100A has an electrode material 110A beneath portions of the sensor element 104 and an electrode material 110B on top of portions of the sensor element 104. In one embodiment, the electrode materials 110A and 110B substantially seal the edges and a portion of a top surface 112 of the sensor element 104 to form a vapor barrier to the absorption of moisture. In such an embodiment, the electrode material 110A/110B may be utilized as a sealant material. In one embodiment, the electrode material 110A may be deposed on the dielectric layer 126 prior to the sensor element 104 being deposed on the dielectric 126. Additionally, in one embodiment, the electrode material 110B may be deposed partially on the sensor element 104 and partially on the electrode material 110A after deposition of the sensor element 104 on the electrode material 110A and the dielectric 126. In one embodiment, the vapor barrier created by the electrode material 110A/110B may reduce volume expansion of the sensor element 104, and may prevent the delamination of the electrode material 110A/110B from the sensor element 104. In one embodiment, an adhesion layer (not shown) may be formed between the electrode material 110A and the sensor element 104. In one embodiment, an adhesion layer (not shown) may be formed between the electrode material 110A and the dielectric 126. In an embodiment, an adhesion layer (not shown) may be formed between the heater material 124 and the dielectric materials 122 and 123 and portions of the electrode material 110A. The adhesion layer may be formed from titanium, chromium, tantalum, or the like.

In one embodiment, the adhesion layer is applied during the same deposition process as the electrode material 110 without breaking the vacuum used during the deposition process and without interrupting the deposition process. Because the electrode material 110 is at least partially enclosed by dielectric materials 123 and 126, as well as, the heater material 124, the adhesion layer may be deposited on both sides of the electrode material 110. For example, the adhesion layer may be deposited, in-situ, both immediately prior to the electrode material 110 (to help the electrode material 110 adhere to the layers directly below the electrode material 110), and immediately after the electrode material 110 (to help the electrode material 110 adhere to the layer formed directly above the electrode material 110).

In one embodiment, the adhesion layer is applied simultaneously with the heater material 124. Because the heater material 124 is enclosed by dielectric materials 123 and 122, as well as, is in intimate contact with electrode material 110, the adhesion layer may be deposited on both sides of the heater material 124. For example, the adhesion layer may be deposited, in-situ, prior to the heater material 124 (to help the heater material 124 adhere to the layers directly below the heater material 124), and after the heater material 124 (to help the heater material 124 adhere to the layers formed directly above the heater material 124). In known prior art it is common to anneal the sensor material 104 at a relatively high temperature. This can cause delamination of the heater material 124 from those films which encapsulate the heater material 124, resulting in a field failure.

The gas detection device 100A is initially formed using the steps described with respect to FIG. 1. The remaining steps for forming the gas detection device 100A are described below. The electrode material 110A is applied simultaneously to the dielectric 126 and onto the contact 128 through dielectric layers 123 and 126 over portions of the heater 124. After electrode material 110A is applied, portions of dielectric 110A are selectively removed, for example by masking and etching, as is known in the art. The sensor element 104 is then deposed over a portion of the electrode material 110A and over a portion of the dielectric 126 through a space 130 formed in the electrode material 110A. The sensor element 104 may be deposed so that a portion of the sensor element 104 is positioned over the electrode material 110A. In the illustrated embodiment, the sensor element 104 is coupled so that the top surface 112 of the sensing material 104 is positioned opposite the substrate 102.

The electrode material 110B is then applied to the sensor element 104 so that the electrode material 110B is applied to at least a part of the top surface 112 (shown in FIG. 4) of the sensor element 104. In one embodiment, the electrode material 110B is coupled to the top surface 112 of the sensing material 104. The electrode material 110B is also applied along a side 132 of the sensor element 104 that extends between the electrode material 110A and the top surface 112 of the sensor element 104. In one embodiment, the electrode material 110B is coupled to the electrode material 110A. For example, the sensor element 104 may have a width that is less than a width of the electrode material 110A so that an exposed section 134 of the electrode material 110A is not covered by the sensor element 104. In such an example, the electrode material 110B may be coupled to portions of the exposed section 134 of the electrode material 110A.

In one embodiment, the electrode material 110A/110B at least partially encapsulates the sensor element 104 to retain the integrity of the interfaces between the sensor element 104 and the electrode material 110A, electrode material 110B, and dielectric material 126 in the event of expansion or contraction of the sensor element 104. It may be noted that a passivating material (not shown) may be selectively applied, or applied then patterned, to passivate portions of the electrode material 110A and 110B, dielectric layer 126, sensor material 104, and other surface layers and features of sensor device 100A. Passivating layers may act, in part, as a moisture barrier, and may also function to mitigate the volume expansion and contraction of the sensor material.

Figure 5:
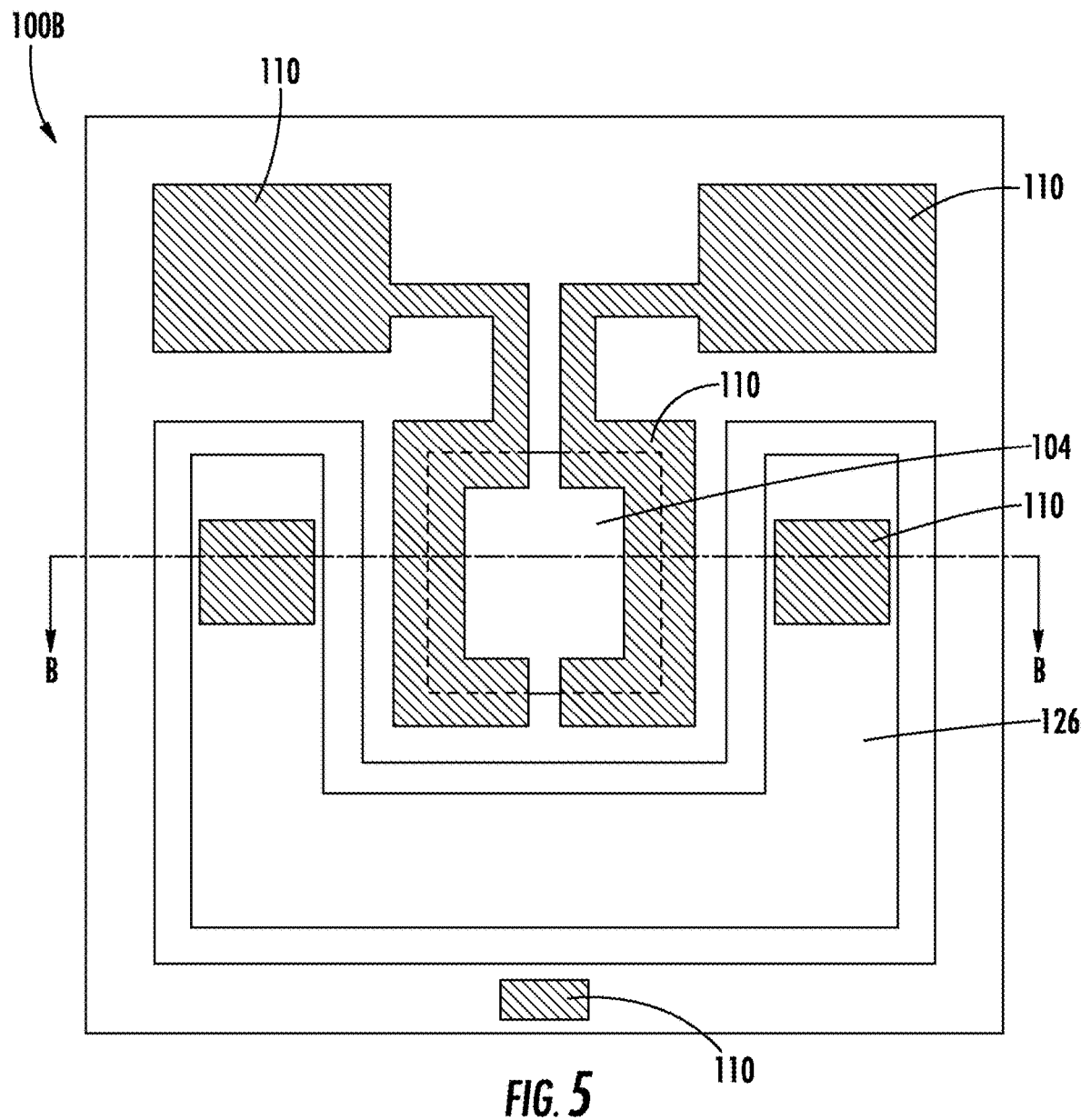
FIG. 5 is a plan view of a gas detector device formed in accordance with an embodiment.
Figure 6:
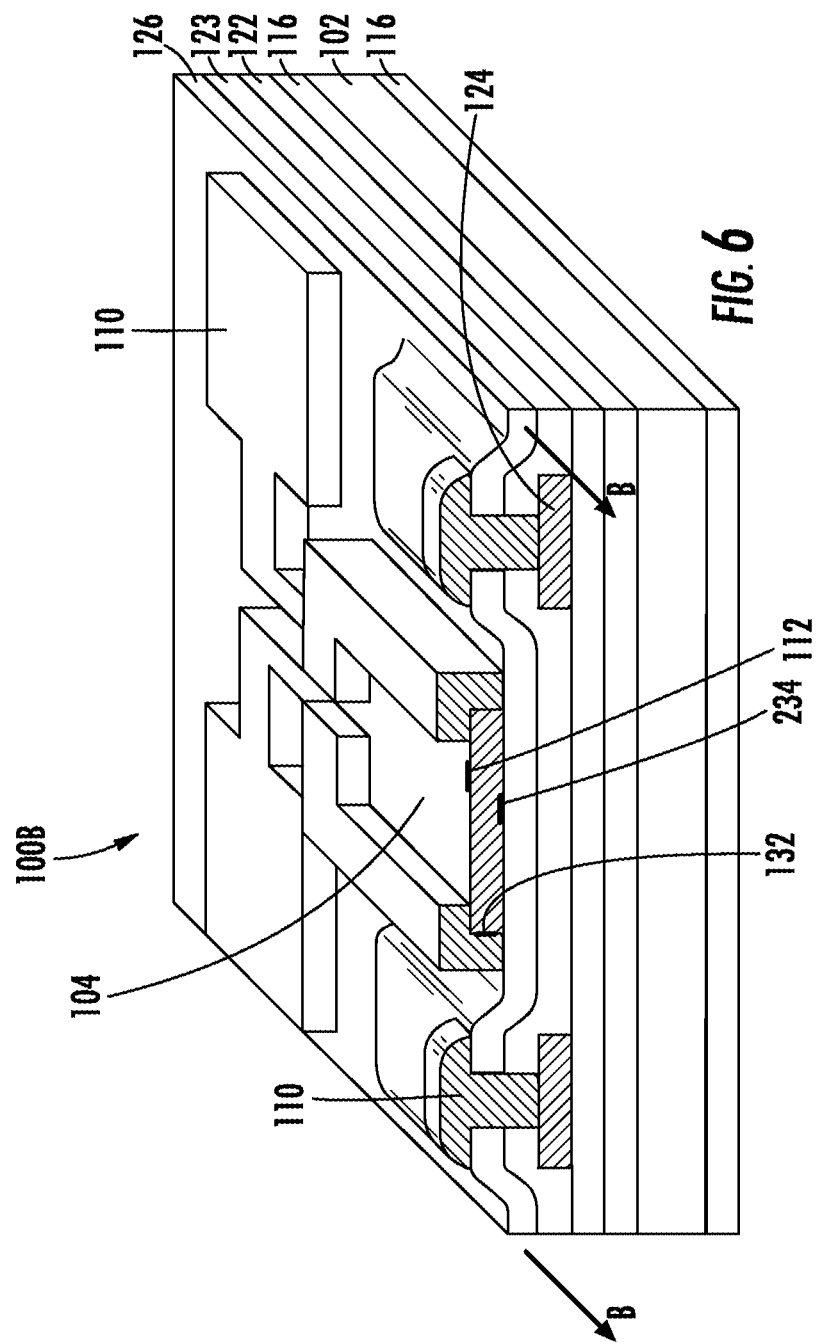
FIG. 6 is a cross sectional isometric view, taken across line B-B of FIG. 5, of a gas detector device formed in accordance with an embodiment.
Figure 7:
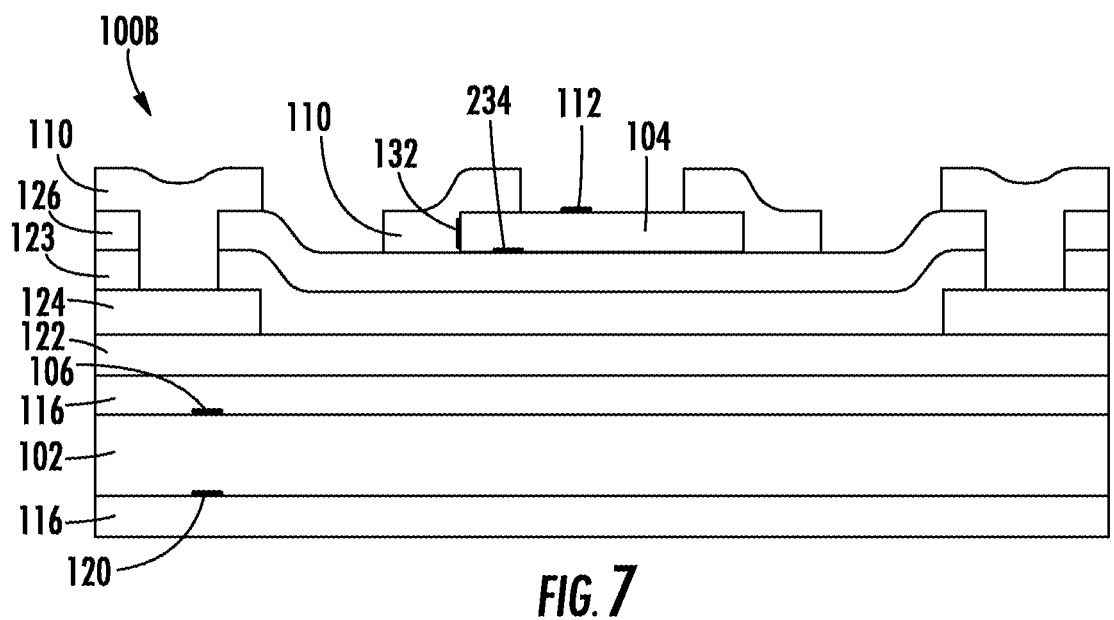
FIG. 7 is a cross sectional view, taken across line B-B of FIG. 5, of a gas detector device formed in accordance with an embodiment.

FIGS. 5-7 illustrate a gas detection device 100B formed from the part of the gas detection device 100 shown in FIG. 1. In such an embodiment, the gas detection device 100B is formed with an electrode material 110 deposed on top of, and not beneath, the sensor element 104. In one embodiment, the gas detection device 100B allows for a single deposition of the electrode material 110. In one embodiment, the electrode material 110 substantially seals the edges of the sensor element 104 to create a vapor barrier by covering at least a portion of the top surface 112 of the sensor element 104 and portions of the sides 132 of sensor element 104 with the electrode material 110. In one embodiment, the gas detection device 100B allows for an entire bottom surface 234 of the sensor material 104 to be in intimate contact with a material on the sensor substrate surface (dielectric 126) to which it adheres well.

In one embodiment, the gas detection device 100B allows for the sensor element 104 to be in contact with a material dielectric 126. In one embodiment, the gas detection device 100B facilitates improving adhesions between the sensor element 104 and the electrode material 110. The sensor element 104 may be substantially pinned to the surface 234 of dielectric 126, even in the presence of another substance which can cause a volume expansion or contraction of the sensor element 104. The structure of the gas detection device 100B substantially provides for the sensor element 104 to be pinned to the surface of dielectric 126, and which facilitates the mitigation of the negative effects of the volume expansion or contraction of the sensor element. In one embodiment, the incidence of delamination between the sensor element 104 and the electrode material 110 may be significantly reduced.

In one embodiment, an adhesion layer (not shown) may be formed between the electrode material 110A and the sensor element 104. In one embodiment, an adhesion layer (not shown) may be formed between the electrode material 110A and the dielectric 126. In one embodiment, an adhesion layer (not shown) may be formed between the heater 124 material and the dielectric materials 122 and 123, as well as portions of the electrode material 110A. The adhesion layer may be formed from titanium, chromium, tantalum, or the like.

The gas detection device 100B is initially formed using the steps described with respect to FIG. 1. The remaining steps for forming the gas detection device 100B are described below. The sensor element 104 is applied to the dielectric 126. In one embodiment, the sensor element 104 is applied to the dielectric 126 using shadow masking. The sensor element 104 is applied to the dielectric 126 so that the top surface 112 of the sensor element 104 is opposite the substrate 102. The electrode material 110 is then applied to the gas detection device 100B. In one embodiment, the electrode material 110 is applied to the gas detection device 100B using shadow masking. The shadow masking advantageously provides for the electrode material 100 to be selectively and simultaneously applied to portions of the top surface 112 of the sensor element 104, on sides 132 of the sensor element 104, to the dielectric 126, into the contact 128 formed within the dielectric materials 123 and 126, and to portions of the heater 124. In one embodiment, the electrode material 110 at least partially encapsulates the sensor element 104 to form a moisture barrier which retains the integrity of the interface between the sensor element 104 and the electrode material 110 in the event of expansion or contraction of the sensor element 104. It may be noted that a passivating material (not shown) may be selectively applied, or applied then patterned, to passivate portions of the electrode material 110, dielectric layer 126, sensor material 104, and other surface layers and features of sensor device 100B. Passivating layers may act, in part, as a moisture barrier, and may also function to mitigate the volume expansion and contraction of the sensor material.

The embodiments described herein include structures (gas detector devices 100A and 100B) and methods of making the structures, wherein the electrode material 110 is deposited upon the structure and then patterned into a useful configuration after the deposition of the sensor element 104, where the processes used to deposit and pattern the electrode material 110 use no water, water-based compounds, water-containing materials, or other saturates, i.e. no water or any other material that causes the sensor element 104 to expand or contract is used to deposit or pattern the electrode material 110, no water is used in the processing after the sensor element 104 is deposited upon the sensor substrate 102. As a result, the sensor element 104 is encapsulated by the electrode material 110 in areas where the sensor element 104 is not pinned to the dielectric layer 126. The embodiments described herein also include a generic base from which the structures are made.

Where the sensor element 104 is pinned to the dielectric layer 126, the sensor element 104 may be exposed to environments which may contain moisture. The pinned portion of the sensor element 104 is bound to the substrate 102 and is not free to fully expand and contract. The electrode material 110 may be used as a vapor barrier, substantially encapsulating the sensor material in those areas where the sensor material is not pinned to the dielectric layer 126.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A gas detection device comprising:
   a substrate;
   a dielectric material applied to the substrate;
   a sensor material applied to the dielectric film, wherein the sensor material has a bottom, a side, and a top surface;
   an electrode material at least partially applied to the dielectric film and at least partially applied to a portion of the bottom of the sensor material, a portion of the side of the sensor material, and a portion of the top surface of the sensor material; and
   an adhesion layer applied during a deposition process with the electrode material.

2. The gas detection device of claim 1, wherein:
   the electrode material at least partially applied to the dielectric film and at least partially applied to the portion of the bottom of the sensor material, the portion of the side of the sensor material, and the portion of the top surface of the sensor material is operable to pin a portion of the sensor material to the dielectric material, wherein the electrode material forms a vapor barrier upon the sensor material to facilitate preventing delamination between the sensor material and the electrode material over portions of the sensor material where the sensor material is not pinned to the dielectric material; and
   the vapor barrier is formed by the electrode material on the portion of the bottom of the sensor material, the portion of the side of the sensor material, and the portion of the top surface of the sensor material where the electrode material is applied.

3. The gas detection device of claim 2, wherein the electrode material substantially encloses portions of the sensor material which are not pinned to the dielectric layer, wherein the electrode material mitigates the volume expansion or contraction of the portions of the sensor material enclosed by the electrode material.

4. The gas detection device of claim 2, wherein the electrode material is constructed and arranged to deform with the volume expansion or contraction of the sensor material without causing the delamination of the electrode material from the sensor material.

5. The gas detection device of claim 2, wherein the electrode material is constructed and arranged to remain in contact with the sensor material during volume expansion or contraction of the sensor material.

6. The gas detection device of claim 2, wherein at least a portion of the electrode material is positioned between the dielectric material and the sensor material.

7. The gas detection device of claim 2, wherein the electrode material is formed without the use of water, water-based compounds, or saturating materials after the sensor material has been formed upon the substrate.

8. The gas detection device of claim 1, wherein the adhesion layer is further applied without breaking a vacuum formed during the deposition process and without interrupting the deposition process.

9. A method of forming a gas detection device comprising:
   applying a dielectric material to a substrate;
   applying a sensor material to the dielectric film, wherein the sensor material has a bottom, a side, and a top surface;
   at least partially applying an electrode material to the dielectric film and a portion of the bottom of the sensor material, a portion of the side of the sensor material, and a portion of the top surface of the sensor material; and
   applying an adhesion layer during a deposition process with the electrode material.

10. The method of claim 9, wherein:
    applying the adhesion layer during the deposition process with the electrode materials to pin a portion of the sensor material to the dielectric material, wherein the electrode material forms a vapor barrier upon the sensor material to facilitate preventing delamination between the sensor material and the electrode material over portions of the sensor material where the sensor material is not pinned to the dielectric material; and
    the method further comprises forming the vapor barrier with the electrode material on the portion of the bottom of the sensor material, the portion of the side of the sensor material, and the portion of the top surface of the sensor material where the electrode material is applied.

11. The method of claim 10 further comprising substantially enclosing, with the electrode material, portions of the sensor material which are not pinned to the dielectric layer, wherein the electrode material mitigates the volume expansion or contraction of the portions of the sensor material enclosed by the electrode material.

12. The method of claim 10 further comprising constructing and arranging the electrode material to deform with the volume expansion or contraction of the sensor material without causing the delamination of the electrode material from the sensor material.

13. The method of claim 10 further comprising constructing and arranging the electrode material to remain in contact with the sensor material during volume expansion or contraction of the sensor material.

14. The method of claim 10 further comprising positioning at least a portion of the electrode material between the dielectric material and the sensor material.

15. The method of claim 10 further comprising forming the electrode material without the use of water, water-based compounds, or saturating materials after the sensor material has been formed upon the substrate.

16. The method of claim 10 further comprising forming the electrode material in more than one deposition step.

17. The method of claim 10 further comprising forming at least one deposition of the electrode material after the deposition of the sensor material.

18. The method of claim 10 further comprising forming at least one deposition of the electrode material after the deposition of the sensor material without the use of water, water based compounds, or saturating materials.

19. The method of claim 9 further comprising applying the adhesion layer without breaking a vacuum formed during the deposition process and without interrupting the deposition process.

\* \* \* \* \*